United States Patent [19]

Dygos

[11] 4,125,544

[45] Nov. 14, 1978

[54] 20/22/23/24-OXA-7-OXOCHOLESTEROLS AND ESTERS THEREOF

[75] Inventor: John H. Dygos, Northbrook, Ill.

[73] Assignee: G. D. Searle, Chicago, Ill.

[21] Appl. No.: 804,951

[22] Filed: Jun. 9, 1977

[51] Int. Cl.$^2$ .................................................. C07J 1/00
[52] U.S. Cl. .............................. 260/397.4; 260/397.1; 260/397.5; 260/239.55 R
[58] Field of Search ........................................ 260/397.4

[56] References Cited

U.S. PATENT DOCUMENTS

| | | | |
|---|---|---|---|
| 3,326,758 | 6/1967 | Ormscher et al. | 260/167.65 |
| 4,006,172 | 2/1977 | Salmond | 260/397.2 |

*Primary Examiner*—Elbert L. Roberts
*Attorney, Agent, or Firm*—John M. Brown

[57] ABSTRACT

Preparation and the antimicrobial and antihypercholesterolemic utility of 20/22/23/24-oxa-7-oxocholesterols and esters thereof are disclosed.

10 Claims, No Drawings

20/22/23/24-OXA-7-OXOCHOLESTEROLS AND ESTERS THEREOF

This invention relates to 20/22/23/24-oxa-7-oxocholesterols, their esters, and processes for the preparation thereof. More particularly, this invention provides new, useful, and unobvious chemical compounds of the formula

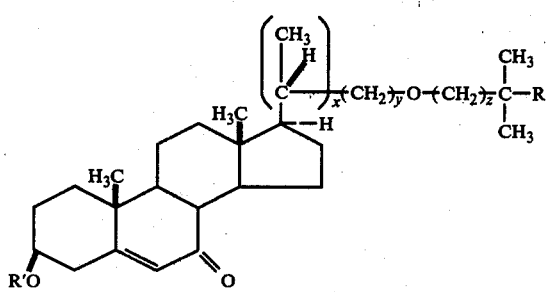

wherein R represents hydrogen or methyl; R' represents hydrogen or 1-oxoalkyl; x represents 0 or 1; y represents 0, 1, or 2; z represents 0, 1, 2, or 3; the sum of the integers represented by x, y, and z is 3; and x represents 0 only when y represents 0.

Among the 1-oxoalkyls represented by R', those containing fewer than 9 carbons are preferred, which is to say formyl and radicals of the formula

wherein the alkyl is methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, or like monovalent, saturated, acyclic, straight- or branched-chain hydrocarbon moiety of the formula

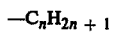

in which n represents a positive integer less than 8.

The compounds to which this invention relates are useful by reason of their valuable biological properties. For example, they are antimicrobial agents adapted to inhibit or prevent the growth of bacteria such as *Neisseira gonorrhoeae* and protozoa such as *Trichomonas vaginalis*. The instant compounds are also antihypercholesterolemic. They suppress the activity of 3-hydroxy-3-methylglutaryl coenzyme A (HMG CoA) reductase, an enzyme which controls the rate at which cholesterol is synthesized in mammalian liver (one of the two principal sources of serum cholesterol).

The antigonnococcal utility of compounds of this invention can be demonstrated as follows: Sufficient compound is dissolved or suspended in melted chocolate agar to afford, upon serial dilution and mixing with additional melted chocolate agar, concentrations of 100, 10, 1, and 0.1 mcgm/ml. The resultant mixtures are permitted to cool and solidify, then surface-inoculated with a suspension of *Neisseira gonnorrhoeae* ATCC 19424 or ATCC 23050. The inoculated mixtures are incubated at 37° C in an atmosphere comprising approximately 10% carbon dioxide for about 48 hours, whereupon they are examined grossly for the presence or absence of test organism growth. Concurrent incubations, identical with the foregoing except that no compound is present, serve as controls. A compound is considered active if, at the maximum concentration tested, no growth of the test organism is visible. Potency is expressed as the minimum concentration at which no growth of the test. The product of Example 3C hereinafter was found active in this test at 10 mcgm/ml against each organism. Potassium penicillin G, inactive in the test as described, was found active against each organism when concentration was increased to 418 mcgm/ml, the procedure being otherwise identical.

The antitrichomonal utility of compounds of this invention can be demonstrated as follows: A modified Diamond medium is prepared by mixing 1200 parts of trypticase (Baltimore Biological Laboratories), 600 parts of yeast extract (Difco), 300 parts of maltose, 60 parts of L-cysteine hydrochloride, 12 parts of L-ascorbic acid, 48 parts of dibasic potassium phosphate, 48 parts of monobasic potassium phosphate, and 54,000 parts of distilled water; adjusting the pH to 6.8 with aqueous 4% sodium hydroxide; incorporating 30 parts of agar (Baltimore Biological Laboratories); boiling for 1 minute to dissolve the agar; and sterilizing, whereupon 80 volumes thereof are diluted with 20 volumes of sterile Dubos medium serum. The resultant medium is inoculated with 1% (by volume) of a 48-hr culture of *Trichomonas vaginalis* ATCC 30001. Meanwhile, compound is heated in sterile distilled water at a concentration of 1000 mcgm/ml for 20 minutes at 80° C. This compound preparation is serially diluted and mixed with sufficient inoculated medium to afford concentrations of 100, 10, 1, and 0.1 mcgm/ml. The mixtures thus obtained are incubated anaerobically for 48 hr at 37° C and examined microscopically for the presence of motile trichomonads. Concurrent incubations, identical with the foregoing except that no compound is present, serve as controls. A compound is considered active if, at the maximum concentration tested, no motile trichomonads are observed and no aberrancy is apparent in respect of the controls. Metronidazole was found active in this test at 1 mcgm/ml; the products of Example 3C and 5C hereinafter were found active at 10 mcgm/ml.

Results of the standardized biological testing of selected compounds of this invention set forth above are provided solely for purposes of illustration, and accordingly should not be considered as either delimiting or exclusionary.

Preparation of the instant compounds proceeds by (1) contacting an oxacholesterol derivative of the formula

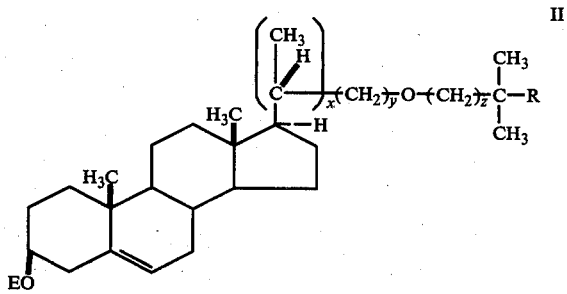

wherein R, x, y, and z are defined as in Formula I and E represents trialkylsilyl, tetrahydro-2H-pyran-2-yl, or 1-oxoalkyl, with a 1:2 mixture of chromium oxide and pyridine in dichloromethane, and (2) heating the corresponding 7-one which eventuates with a weak acid in tetrahydrofuran if the 7-one is a 3-ether, or with aqueous bicarbonate in methanol if it is a 3-ester. The resultant 3-ol can be converted to a 3-alkanoate of this invention by contacting it with an alkanoic acid anhydride or halide in pyridine.

A preferred method of preparing an oxacholesterol derivative of Formula II comprises heating an alcohol of the formula

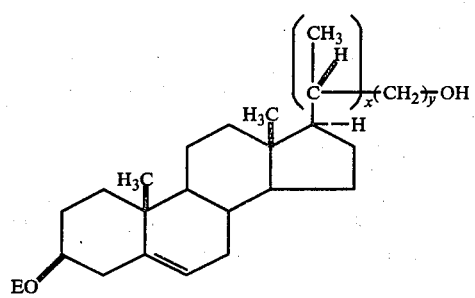

III with an alkali metal hydride in a mixture of dimethylbenzenes to produce the corresponding alkoxide, which is heated in situ with a haloalkane of the formula

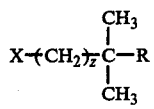

IV

In formula III, E is defined as in Formula II, $x$ represents 0 or 1; $y$ represents 0, 1, or 2; and $x$ represents 0 only when $y$ represents 0. In Formula IV, X represents halogen - preferably bromine; $z$ represents 0, 1, or 2; and R represents hydrogen when $z$ represents 0, otherwise it is defined as in Formula I.

Another method of preparing an oxacholesterol of Formula II comprises heating an alcohol of Formula III with an alkali metal hydride in a mixture of dimethylbenzenes to produce the corresponding alkoxide, which is heated in situ with an alkyl mesylate of the formula

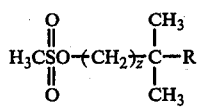

V product Example was
wherein R and $z$ are defined as in Formula IV.

Still another method of preparing an oxacholesterol of Formula II comprises dissolving potassium in liquid ammonia containing a catalytic amount of ferric ion to produce potassium amide, which is contacted in situ with an alcohol of Formula III to produce the corresponding alkoxide, which in turn is contacted in situ with a haloalkane of Formula IV.

An alternative method for preparing an oxacholesterol of Formula II wherein $x$ represents 1; $y$ represents 1 or 2; $z$ represents 0 or 1; the sum of the integers represented by $x$, $y$, and $z$ is 3; and R represents hydrogen or methyl except when $z$ represents 0, in which instance R represents solely hydrogen, comprises contacting an alkanol of Formula III wherein $x$ represents 1 and $y$ represents 1 or 2 with a methanesulfonyl halide in pyridine to produce the corresponding mesylate, which is heated in a mixture of dimethylbenzenes with the alkoxide which eventuates upon heating an alkanol of the formula

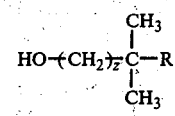

VI with an alkali metal hydride therein, $z$ and R in Formula VI being defined as immediately preceding.

An alternative method for preparing an oxacholesterol of Formula II wherein $x$ represents 1, $y$ represents 2, $z$ represents 0, and R represents hydrogen, comprises contacting 1-methylethyl 3β-hydroxy-24-norchol-5-en-23-oate with a combination of trifluoroborane and sodium tetrahydroborate(1-) in 1,1'oxybis[2-methoxyethane] and tetrahydrofuran according to the procedure illustrated in Example 20 of U.S. Pat. No. 3,326,758, and esterifying or etherifying the resultant 3-ol to introduce a moiety represented by E in Formula II via contact with (1) an alkanoic acid anhydride or halide in pyridine, (2) a trialkylchorosilane such as chlorotrimethylsilane, chlorotriethylsilane, or — preferably — chloro(1,1-dimethylethyl)dimethylsilane in the presence of a weak base such as imidazole, using N,N-dimethylformamide as the reaction medium, or (3) 3,4-dihydro-2H-pyran in the presence of a catalytic amount of 4-methylbenzenesulfonic or other acid, using tetrahydrofuran as the reaction medium.

As an exception to the foregoing methods for preparing an oxacholesterol of Formula II, when $x$, $y$, and $z$ represent 1, 2, and 0, respectively, and R represents methyl therein, the preferred preparation comprises contacting 3β-(acetyloxy)-24-norchol-5-en-23-ol with 2-methyl-1-propene in the presence of a catalytic amount of sulfuric acid (for which a 1:1 complex of trifluoroborane and phosphoric acid can be substituted if desired) using cold dichloromethane as the reaction medium. The resultant 3-acetate can be hydrolyzed by heating it with aqueous bicarbonate in methanol, and the 3-ol thus obtained reesterified or etherified to introduce any moiety represented by E in Formula II via the procedures hereinbefore referred to.

The alcohols of Formula III can be prepared via appropriate selection from among such procedures as those described in J. Org. Chem., 38, 4209 (1973); Steroids, 7, 557 (1966); Bull. soc. chim. France, 1972, 2344; J. Chem. Soc. Perkin I. 1975, 2302; and J. Med. Chem., 20, 5 (1977).

The following examples described in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. The oil is removed from 20 parts of a 50% dispersion of sodium hydride in mineral oil by slurrying the dispersion with a mixture of dimethylbenzenes in a nitrogen atmosphere and then decanting the solvent, whereupon 450 parts of a mixture of dimethylbenzenes followed by a warm solution of 100 parts of 3β-{[(1,1-dimethylethyl)dimethylsilyl]oxy}androst-5-en-17β-ol in 900 parts of a mixture of dimethylbenzenes is added, with stirring under nitrogen, to the sodium hydride. The resultant mixture is refluxed with stirring under nitrogen for 1½ hours and then cooled to room temperature, at which point a solution of 66 parts of 1-bromo-4-methylpentane in 450 parts of a mixture of dimethylbenzenes is added. The mixture thus obtained is refluxed with stirring under nitrogen for 6 hours, then cooled, and finally diluted with an equal volume of 1,1'-oxybisethane, whereupon insoluble solids are filtered out and washed on the filter with 1400 parts of 1,1'-oxybisethane. The filtrate is stripped of solvent by vacuum distillation, and the residue is recrystallized from a mixture of 1,1'-oxybisethane and methanol to give 3β-{[(1,1-dimethylethyl)dimethylsilyl]oxy}-17β-[(4-methylphenyl)oxy]androst-5-ene melting at approximately 137°-138°. The product has the formula

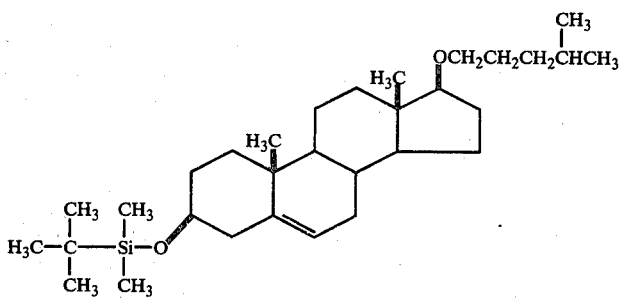

B. To a solution of 58 parts of pyridine in 1100 parts of dichloromethane under a nitrogen atmosphere is added, with stirring at room temperature, 37 parts of chromium oxide. The resultant mixture is stirred at room temperature under nitrogen for approximately ½ hour, whereupon a solution of 9 parts of 3β-{[(1,1-dimethylethyl)dimethylsilyl]oxy}-17β-[(4-methylpentyl)oxy]androst-5-ene in 200 parts of dichloromethane is stirred in. Stirring at room temperature under nitrogen is continued for 20 hours, at which point liquid supernatant is separated by decantation, residual solids are extracted with dichloromethane, the extract is combined with the supernatant, and solvent is removed from the combined liquids by vacuum distillation. The dark residue is extracted with hot 1,1'-oxybisethane, and the extract is filtered through diatomaceous earth. The filtrate is stripped of solvent by vacuum distillation; and the residue is chromatographed on silica gel, using 2% ethyl acetate in benzene as developing solvent. Eluates are selected via thin layer chromatography which, upon evaporation of solvent and recrystallization of the residues from a mixture of 1,1β-oxybisethane and methanol, afford 3β-{[(1,1-dimethylethyl)dimethylsilyl]oxy}-17β-[(4-methylpentyl)oxy]androst-5-en-7-one melting at 143°-145°.

C. A mixture of 3 parts of 3β-{(1,1-dimethylethyl)-dimethylsilyl]oxy}-17β-[(4-methylpentyl)oxy]androst-5-en-7-one, 45 parts of tetrahydrofuran, 15 parts of acid, and 10 parts of water is heated at approximately 60° for 48 hours, whereupon 300 parts of water is added and the resultant mixture is extracted with 1,1'-oxybisethane. The extract is washed with aqueous 5% potassium bicarbonate, dried over magnesium sulfate, and strippd of solvent by vacuum distillation. The residue is chromatographed on silica gel, using mixtures of benzene and ethyl actate (initially comprising 10% ethyl acetate and progressively increasing the proportions thereof to 25%) as developing solvent. Eluates are selected via thin layer chromatography which, upon evaporation of solvent and recrystallization of the residues from a mixture of 1,1'-oxybisethane and hexane, afford 3β-hydroxy-17β-[(4-methylpentyl)oxy]androst-5en-7-one melting at approximately 133.5°-134.5°. The product has the formula

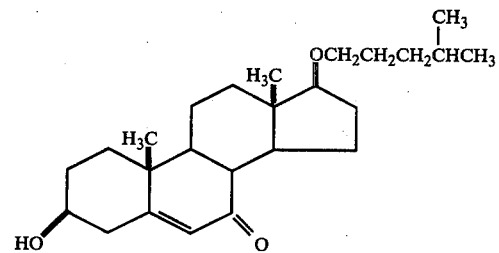

EXAMPLE 2

A. A solution of 14 parts of methanesulfonyl chloride in 50 parts of pyridine is added, with stirring, to a solution of 12 parts of 4,4-dimethylpentanol in 50 parts of pyridine at approximately 0°. The resultant mixture is warmed to room temperature and maintained thereat for 1 hour with continued stirring, then poured into 700 parts of water. The mixture thus obtained is extracted with 1,1'-oxybisethane. The extract is consecutively washed with 5% hydrochloric acid and aqueous 5% potassium bicarbonate, then dried over magnesium sulfate, and thereupon stripped of solvent by vacuum distillation. The residual yellow oil is 4,4-dimethylpentyl methanesulfonate, having the formula

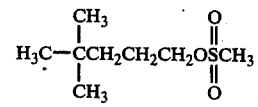

B. The oil is removed from 25 parts of a 50% dispersion of sodium hydride in mineral oil by slurrying the dispersion with a mixture of dimethylbenzenes in a nitrogen atmosphere and then decanting the solvent, whereupon 450 parts of a mixture of dimethylbenzenes followed by a warm solution of 101 parts of 3β-{[(1,1-dimethylethyl)dimethylsilyl]androst-5-en-17β-ol in 900 parts of a mixture of dimethylbenzenes is added, with stirring under nitrogen, to the sodium hydride. The resultant mixture is refluxed with stirring under nitrogen for 1¼ hours and then cooled to room temperature, at which point a solution of 70 parts of 4,4-dimethylpentyl methanesulfonate in 450 parts of a mixture of dimethylbenzenes is added. The mixture thus obtained is refluxed with stirring under nitrogen for 6 hours, then cooled, and finally diluted with an equal volume of 1,1'-oxybisethane, whereupon insoluble solids are filtered out and washed on the filter with 1400 parts of 1,1'-oxybisethane. The filtrate is stripped of solvent by vacuum distillation; and the residue is chromatographed on silica gel, using 57% benzene in hexane as developing solvent. Eluates are selected via thin layer chromatography which, upon evaporation of solvent and recrystallization of the residues from a mixture of 1,1'-oxybisethane and methanol, afford 3β-{[(1,1-dimethylethyl)dimethylsilyl]oxy}-17β-[(4,4-dimethylpentyl)oxy]androst-5-ene melting at approximately 138°–139°.

C. To a solution of 13 parts of pyridine in 335 parts of dichloromethane under a nitrogen atmosphere is added, with stirring at room temperature, 8 parts of chromium oxide. The resultant mixture is stirred at room temperature under nitrogen for approximately ½ hour, whereupon a solution of 2 parts of 3β-{[(1,1-dimethyl-ethyl)-dimethylsilyl]oxy}-17β-[(4,4-dimethylpentyl)oxy]-androst-5-ene in 65 parts of dichloromethane is stirred in. Stirring at room temperature under nitrogen is continued for 18 hours, at which point liquid supernatant is separated by decantation, residual solids are extracted with dichloromethane, the extract is combined with the supernatant, and solvent is removed from the combined liquids by vacuum distillation. The residue is extracted with hot 1,1'-oxybisethane, and the extract is filtered through diatomaceous earth. The filtrate is stripped of solvent by vacuum distillation; and the residue is chromatographed on silicic acid, using hexane, mixtures thereof with increasing amounts of benzene, and finally benzene alone as developing solvent. Eluates are selected via thin layer chromatography which, upon evaporation of solvent and recrystallization of the residues from a mixture of 1,1'-oxybisethane and methanol, afford 3β-{[(1,1-dimethylethyl)dimethylsilyl]oxy}-17β-[(4,4-dimethylpentyl)oxy]androst-5-en-7-one melting at approximately 155°–156°.

D. A mixture of 1 part of 3β-{[(1,1-dimethylethyl)dimethylsilyl]oxy}-17β-[(4,4-dimethylpentyl)oxy]androst-5-en-7-one, 22 parts of tetrahydrofuran, 10 parts of acetic acid, and 5 parts of water is heated at approximately 60° under reflux for 48 hours, then poured into 200 parts of water. Approximately 15 parts of sodium chloride is stirred into the resultant mixture. The solid which precipitates is isolated by filtration, washed on the filter with water, dried in air, and finally taken up in 1,1'-oxybisethane. Solvent is thereupon removed by vacuum distillation; and the residue is chromatographed on silicic acid, using benzene and mixtures thereof with increasing amounts of ethyl acetate as developing solvent. Eluates are selected via thin layer chromatography which, upon evaporation of solvent and recrystallization of the residues from a mixture of 2-propanone and hexane, afford 3β-hydroxy-17β-[(4,4-dimethylpentyl)oxy]androst-5-en-7-one melting at 203°–205°. The product has the formula

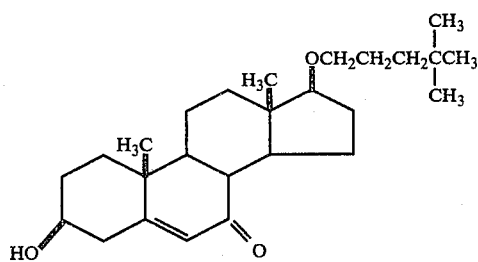

EXAMPLE 3

A. The oil is removed from 6 parts of a 50% dispersion of sodium hydride in mineral oil by slurrying the dispersion with a mixture of dimethylbenzenes in a nitrogen atmosphere and then decanting the solvent, whereupon 1800 parts of a mixture of dimethylbenzenes followed by a warm solution of 30 parts of 3β-[(tetrahydro-2H-pyran-2-yl)oxy]pregn-5-en-20S-ol ]Steroids, 7,557, (1966)] in 265 parts of tetrahydrofuran is added, with stirring under nitrogen, to the sodium hydride. The resultant mixture is refluxed with stirring under nitrogen for 1 hour and then cooled to room temperature, at which point a solution of 80 parts of 1-bromo-3-methylbutane in 545 parts of a mixture of dimethylbenzenes is added. The mixture thus obtained is refluxed with stirring under nitrogen for 6 hours, then cooled, and finally diluted with an equal volume of 1,1'-oxybisethane, whereupon insoluble solids are filtered out and washed on the filter with 1,1'-oxybisethane. The combined filtrate and wash is stripped of solvent by vacuum distillation; and the residue is chromatographed on silicic acid, using benzene and mixtures thereof with increasing amounts of ethyl acetate as developing solvent. Eluates are selected via thin layer chromatography which, upon evaporation of solvent and recrystallization of the residues from methanol, afford 20S-(3-methylbutoxy)-3β[(tetrahydro-2H-pyran-2-yl)oxy[pregn-5-ene melting at 104°–106°. The product has the formula

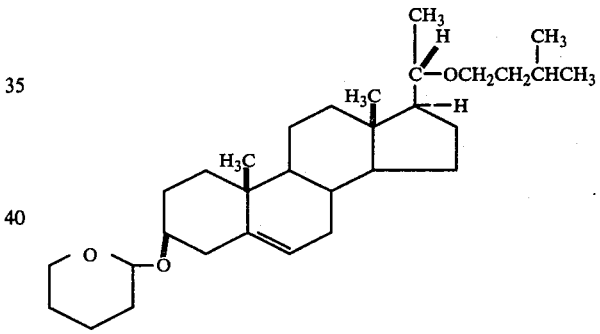

B. To a solution of 21 parts of pyridine in 270 parts of dichloromethane under a nitrogen atmosphere is added, with stirring at room temperature, 13 parts of chromium oxide. The resultant mixture is stirred at room temperature under nitrogen for approximately ½ hour, whereupon a solution of 3 parts of 20S-(3-methylbutoxy)-3β-[(tetrahydro-2H-pyran-2-yl)oxy]pregn-5-ene in 130 parts of dichloromethane is added. Stirring at room temperature uner nitrogen is continued for 20 hours, at which point liquid supernatant is separated by decantation, residual solids are extracted with dichloromethane, the extract is combined with the supernatant, and solvent is removed from the combined liquids by vacuum distillation. The residue is extracted with hot 1,1'-oxybisethane, and the extract is filtered through diatomaceous earth. The filtrate is stripped of solvent by vacuum distillation; and the yellow residue is chromatographed on silica gel, using 5% ethyl acetate in benzene as developing solvent. Eluates are selected via thin layer chromatography which, combined and stripped of solvent by vacuum distillation, afford 20S-(3-methylbutoxy)-3β-[(tetrahydro-2H-pyran-2-yl)oxy]pregn-5-en-7-one as the residue C. A mixture of 6 parts of 20S-(3-methylbutoxy)-3β-[(tetrahydro-2H-pyran-2-yl)oxy]pregn-5-en-7-one, 90 parts of tetrahydrofuran, 50 parts of acetic acid, and 30 parts of water is heated at approximately 60° for 48 hours, then poured into 1200 parts of water. The resultant mixture is extracted with dichloromethane. The dichloromethane extract is washed with aqueous 5% potassium bicarbonate, dried over magnesium sulfate, and stripped of solvent by vacuum distillation. The residue is chromatographed on silicic acid, using benzene and mixtures thereof with increasing amounts of ethyl acetate as developing solvent. Eluates are selected via thin layer chromatography which, upon evaporation of solvent and recrystallization of the residues from a mixture of 1,1'-oxybisethane and hexane, afford 20S-(3-methylbutoxy)-3β-hydroxypregn-5-en-7-one melting at 119°-121°. The product has the formula

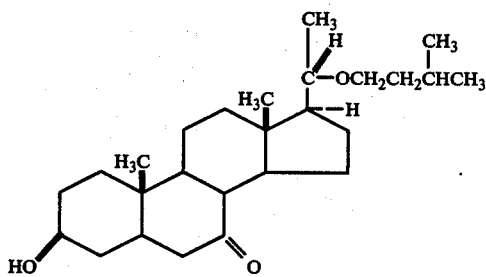

EXAMPLE 4

A. To a solution of 6 parts of 3,3-dimethyl-1-butanol in 75 parts of pyridine at 0° is added, with stirring, 8 parts of methanesulfonyl chloride. The resultant mixture is allowed to warm to room temperature and maintained thereat with continuous stirring for 3 hours, then poured into 500 parts of water. The mixture thus obtained is extracted with 1,1'-oxybisethane. The extract is consecutively washed with 5% hydrochloric acid and aqueous 5% potassium bicarbonate, then dried over magnesium sulfate, and finally stripped of solvent by vacuum distillation. The residue is 3,3-dimethylbutyl methanesulfonate.

B. The oil is removed from 1 part of a 50% dispersion of sodium hydride in mineral oil by slurrying the dispersion with a mixture of dimethylbenzenes in a nitrogen atmosphere and then decanting the solvent, whereupon 65 parts of a mixture of dimethylbenzenes followed by a warm solution of 3 parts of 3β-[(tetrahydro-2H-pyran-2-yl)oxy]pregn-5-en-20S-ol in 65 parts of a mixture of dimethylbenzenes is added, with stirring under nitrogen, to the sodium hydride. The resultant mixture is refluxed with stirring under nitrogen for 1 hour and then cooled to room temperature, at which point a solution of 4 parts of 3,3-dimethylbutyl methanesulfonate in 20 parts of a mixture of dimethylbenzenes is added. The mixture thus obtained is refluxed with stirring under nitrogen for 6 hours, then cooled, and finally diluted with 100 parts of 1,1'-oxybisethane, whereupon insoluble solids are removed by filtration via diatomaceous earth. The filtrate is stripped of solvent by vacuum distillation; and the residue is chromatographed on silica gel, using benzene as developing solvent. Eluates are selected via thin layer chromatography which, upon evaporation of solvent and recrystallization of the residues from a mixture of 1,1'-oxybisethane and methanol, afford 20S-(3,3-dimethylbutoxy)-3β-[(tetrahydro-2H-pyran-2-yl)oxy]pregn-5-ene melting at 125°-127°.

To a solution of 21 parts of pyridine in 480 parts of dichloromethane under a nitrogen atmosphere is added, with stirring at room temperature, 13 parts of chromium oxide. The resultant mixture is stirred at room temperature under nitrogen for approximately ½ hour, whereupon a solution of 3 parts of 20S-(3,3-dimethylbutoxy)-3β-[(tetrahydro-2H-pyran-2-yl)oxy]pregn-5-ene in 130 parts of dichloromethane is stirred in. Stirring at room temperature under nitrogen is continued for 20 hours, at which point liquid supernatant is separated by decantation, residual solids are extracted with dichloromethane, the extract is combined with the supernatant, and the solvent is removed from the combined liquids by vacuum distillation. The residue is extracted with hot 1,1'-oxybisethane, and the extract is filtered through diatomaceous earth. The filtrate is stripped of solvent by vacuum distillation; and the residue is chromatographed on silica gel, using mixtures of benzene and ethyl acetate (initially comprising 2% ethyl acetate and progressively increasing the proportions thereof) as developing solvent. Eluates are selected via thin layer chromatography which, combined and stripped of solvent by vacuum distillation, afford 20S-(3,3-dimethylbutoxy)-3β-[(tetrahydro-2H-pyran-2-yl)oxy]-7-one as the residue. The product has the formula

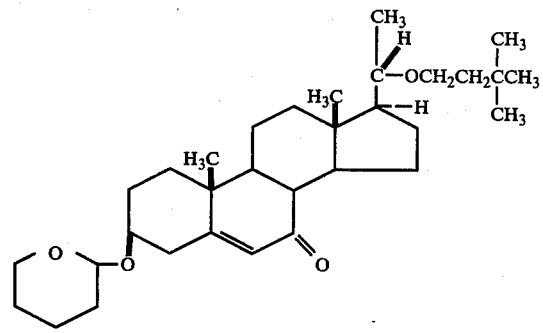

D. A mixture of 3 parts of 20S-(3,3-dimethylbutoxy)-3β-[(tetrahydro-2H-pyran-2-yl)oxy]pregn-5-en-7-one, 180 parts of tetrahydrofuran, 100 parts of acetic acid, and 30 parts of water is heated at approximately 60° under reflux for 3 hours, whereupon it is poured into 1600 parts of water. To the resultant mixture, 120 parts of sodium chloride is added. The solid which precipitates is isolated by filtration, washed with water, and dried in air, then taken up in dichloromethane. The dichloromethane extract is washed with aqueous 5% potassium bicarbonate, dried over magnesium sulfate, and stripped of solvent by vacuum distillation. The residue is chromatographed on silica gel, using 20% ethyl acetate in benzene as developing solvent. Eluates are selected via thin layer chromatography which, upon evaporation of solvent and recrystallization of the residues from a mixture of 1,1'-oxybisethane and hexane, afford 20S-(3,3-dimethylbutoxy)-3β-hydroxypregn-5-en-7-one melting at 141°-143°. The product has the formula

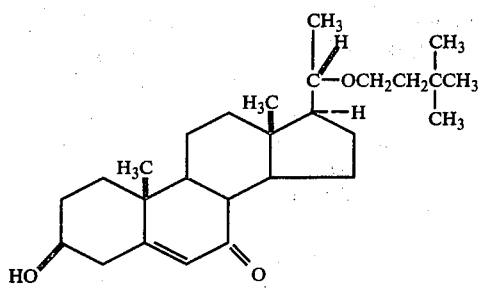

EXAMPLE 5

A. A mixture of 3 parts of 20S-methyl-22-(2-methylpropoxy)pregn-5-en-3β-ol [U.S. Pat. No. 3,326,758 (Ex. 19)], 2 parts of chloro(1,1-dimethylethyl)dimethylsilane, 2 parts of 1H-imidazole, and 75 parts of N,N-dimethylformamide is stirred until solution is complete, then allowed to stand at room temperature for 3 hours, and thereupon diluted with 300 parts of 1,1'-oxybisethane. The resultant solution is washed with water, dried over magnesium sulfate, and stripped of solvent by vacuum distillation. The residue is chromatographed on silicic acid, using hexane and mixtures thereof with increasing amounts of benzene as developing solvent. Eluates are selected by thin layer chromatography which, upon evaporation of solvent and recrystallization of the residues thus obtained from a mixture of 1,1'-oxybisethane and methanol, afford 3β-{[(1,1-dimethylethyl)dimethylsilyl]oxy}-20S-methyl-22-(2-methylpropoxy)pregn-5-ene melting at 163.5°–165°. The product has the formula

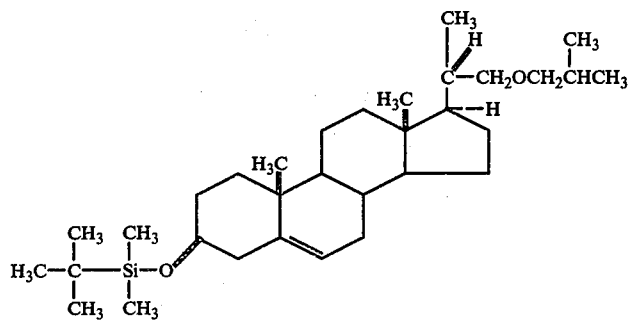

B. To a solution of 19 parts of pyridine in 400 parts of dichloromethane under a nitrogen atmosphere is added, with stirring at room temperature, 12 parts of chromium oxide. The resultant mixture is stirred at room temperature under nitrogen for approximately ½ hour, whereupon a solution of 3 parts of 20S-methyl-22-(2-methylpropoxy)pregn-5-en-3β-ol in 135 parts of dichloromethane is stirred in. Stirring at room temperature under nitrogen is continued for 18 hours, at which point liquid supernatant is separated by decantation, residual solids are extracted with dichloromethane, the extract is combined with the supernatant, and solvent is removed from the combined liquids by vacuum distillation. The residue is extracted with hot 1,1'-oxybisethane, and the extract is filtered through diatomaceous earth. The filtrate is stripped of solvent by vacuum distillation; and the residue is chromatographed on silica gel, using benzene as developing solvent. Eluates are selected via thin layer chromatography which, combined and stripped of solvent by vacuum distillation, afford 3β-{[1,1'-dimethylethyl)dimethylsilyl]oxy}-20S-methyl-22-(2-methylpropoxy)pregn-5-en-7-one as the residue.

C. A mixture of 3 parts of 3β-{[(1,1-dimethylethyl)dimethyl]oxy}-20S-methyl-22-(2-methylpropoxy)-pregn-5-en-7-one, 70 parts of tetrahydrofuran, 24 parts of acetic acid, and 16 parts of water is heated at approximately 60° under reflux for 48 hours, whereupon 300 parts of water is added; and the resultant mixture is extracted with 1,1'-oxybisethane. The extract is washed with aqueous 5% potassium bicarbonate, dried over magnesium sulfate, and stripped of solvent by vacuum distillation. The residue is chromatographed on silica gel, using 15% ethyl acetate in benzene as developing solvent. Eluates are selected via thin layer chromatography which, upon evaporation of solvent and recrystallization of the residues from cold pentane, afford 3β-hydroxy-20S-methyl-22-(2-methylpropoxy)pregn-5-en-7-one. The product has the formula

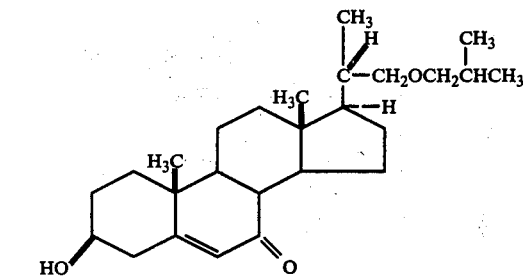

EXAMPLE 6

A. To a solution of 2 parts of 20S-methyl-3β-[(tetrahydro-2H-pyran-2-yl)oxy]pregn-5-en-22-ol (J. Chem. Soc. Perkin I, 1975, 2302) in 10 parts of pyridine is slowly added a solution of 1 part of methanesulfonyl chloride in 10 parts of pyridine. The resultant mixture is stirred at room temperature for 1 hour, then poured into 100 parts of water. The solid which precipitates is isolated by filtration, washed with water, air-dried, and finally taken up in dichloromethane. The dichloromethane solution is dried over magnesium sulfate and then stripped of solvent by vacuum distillation. The residue is 20S-methyl-3β-[(tetrahydro-2H-pyran-2-yl)oxy]-pregn-5-en-22-yl methanesulfonate, having the formula

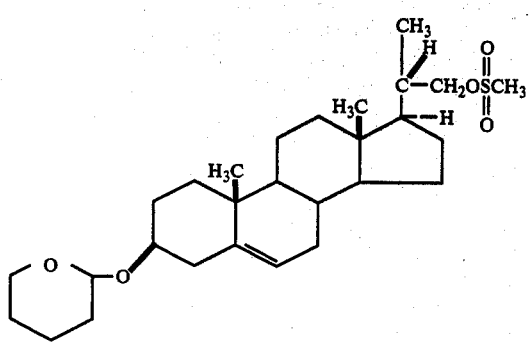

B. The oil is removed from 1 part of a 50% dispersion of sodium hydride in mineral oil by slurrying the dispersion with a mixture of dimethylbenzenes in a nitrogen atmosphere and then decanting the solvent, whereupon 90 parts of a mixture of dimethylbenzenes followed by a mixture of 2 parts of 2,2-dimethyl-1-propanol is added, with stirring under nitrogen, to the sodium hydride. The resultant mixture is refluxed with stirring under nitrogen for 1 hour and then cooled to room temperature, at which point a solution of 5 parts of 20S-methyl-3β-[(tetrahydro-2H-pyran-2-yl)oxy]pregn-5-en-22-yl methanesulfonate in 90 parts of a mixture of dimethylbenzenes is added. The mixture thus obtained is refluxed with stirring under nitrogen for 6 hours, then cooled, and finally diluted with an equal volume of 1,1′-oxybisethane, whereupon insoluble solids are filtered out and washed on the filter with 1,1′-oxybisethane. The filtrate is stripped of solvent by vacuum distillation; and the residue is chromatographed on silica gel, using 2% ethyl acetate in benzene as developing agent. Eluates are selected via thin layer chromatography which, combined and stripped of solvent by vacuum distillation, afford 22-(2,2-dimethylpropoxy)-20S-methyl-3β-[(tetrahydro-2H-pyran-2-yl)oxy]pregn-5-ene as the residue. The product thus isolated melts at 156°–158°.

C. To a solution of 15 parts of pyridine in 340 parts of dichloromethane under a nitrogen atmosphere is added, with stirring at room temperature, 8 parts of chromium oxide. The resultant mixture is stirred at room temperature under nitrogen for ½ hour, whereupon a solution of 2 parts of 22-(2,2-dimethylpropoxy)-20S-methyl-3β-[(tetrahydro-2H-pyran-2-yl)oxy]pregn-5-ene in 60 parts of dichloromethane is stirred in. Stirring at room temperature under nitrogen is continued for 22 hours, at which point liquid supernatant is separated by decantation, residual solids are extracted with dichloromethane, the extract is combined with the supernatant, and solvent is removed from the combined liquids by vacuum distillation. The residue is taken up in hot 1,1′-oxybisethane, and the resultant solution is filtered through diatomaceous earth. The filtrate is stripped of solvent by vacuum distillation. The residue is 22-(2,2-dimethylpropoxy)-20S-methyl-3β-[(tetrahydro-2H-pyran-2-yl)oxy]pregn-5-en-7-one.

D. A mixture of 3 parts of 22-(2,2-dimethylpropoxy)-20S-methyl-3β-[(tetrahydro-2H-pyran-2-yl)oxy]pregn-5-en-7-one, 18 parts of tetrahydrofuran, 8 parts of acetic acid, and 5 parts of water is heated at approximately 60° under reflux for 4 hours, whereupon it is poured into 200 parts of water. The resultant mixture is extracted with 1,1′-oxybisethane. The extract is washed with aqueous 5% potassium bicarbonate, dried over magnesium sulfate, and stripped of solvent by vacuum distillation. The residue is chromatographed on silica gel, using mixtures of benzene and ethyl acetate (initially comprising 5% ethyl acetate and progressively increasing the proportion thereof) as developing solvent. Eluates are selected via thin layer chromatography which, upon evaporation of solvent and recrystallization of the residues from a mixture of 1,1′-oxybisethane and hexane, afford 22-(2,2-dimethylpropoxy)-3β-hydroxy-20S-methylpregn-5-en-7-one softening at 160° and melting at 165°–167°. The product has the formula

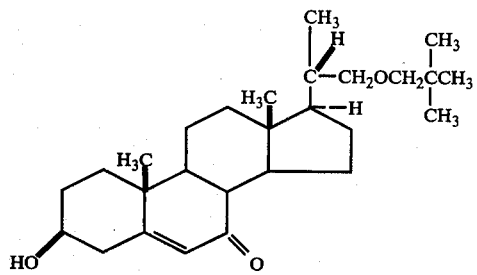

EXAMPLE 7

A. A mixture of 1 part of 3β-hydroxy-23-(1-methylethoxy)-24-norchol-5-ene [U.S. Pat. No. 3,326,758 (Ex. 20)], 5 parts of acetic anhyride, and 10 parts of pyridine is allowed to stand at room temperature overnight, then poured into 120 parts of 5% hydrochloric acid. The resultant mixture is extracted with 1,1′-oxybisethane. The extract is dried over magnesium sulfate and stripped of solvent by vacuum distillation. The residue is 3β-(acetyloxy)-23-(1-methylethoxy)-24-norchol-5-ene, having the formula

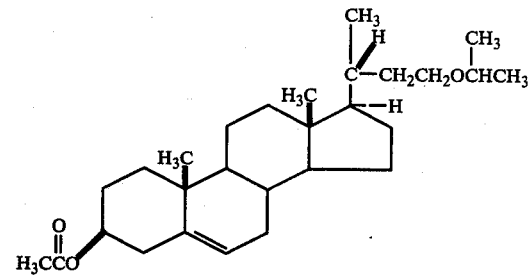

B. To a solution of 15 parts of pyridine in 340 parts of dichloromethane under a nitrogen atmosphere is added, with stirring at room temperature, 8 parts of chromium oxide. The resultant mixture is stirred at room temperature under nitrogen for ½ hour, whereupon a solution of 3 parts of 3β-(acetyloxy)-23-(1-methylethoxy)-24-norchol-5-ene in 60 parts of dichloromethane is stirred in. Stirring at room temperature under nitrogen is continued for 22 hours, at which point liquid supernatant is separated by decantation, residual solids are extracted with dichloromethane, the extract is combined with the supernatant, and solvent is removed from the combined liquids by vacuum distillation. The residue is extracted with hot 1,1′-oxybisethane, and the extract is filtered through diatomaceous earth. The filtrate is stripped of solvent by vacuum distillation. The residue is 3β-(acetyloxy)-23-(1-methylethoxy)-24-norchol-5-en-7-one.

C. A mixture of 7 parts of 3β-(acetyloxy)-23-(1-methylethoxy)-24-norchol-5-en-7-one, 50 parts of aqueous 5% potassium bicarbonate, and 320 parts of methanol is heated at approximately 60° for 2 hours, whereupon most of the methanol is removed by vacuum distillation and the distilland then poured into 1000 parts of 5% hydrochloric acid. The resultant mixture is extracted with 1,1'-oxybisethane. The extract is dried over magnesium sulfate and stripped of solvent by vacuum distillation. The residual dark oil is chromatographed on silicic acid, using benzene and mixtures thereof with increasing amounts of ethyl acetate as developing solvent. Eluates comprising 40% ethyl acetate are combined and stripped of solvent by vacuum distillation, affording 3β-hydroxy-23-(1-methylethoxy)-24-norchol-5-en-7-one as a residual yellow glass, which is chromatographed on silica gel, using 20% ethyl acetate in benzene as developing solvent. Eluates are selected via thin layer chromatography which, upon evaporation of solvent and recrystallization of the residues from 1,1'-oxybisethane, afford 3β-hydroxy-23-(1-methylethoxy)-24-norchol-5-en-7-one as a crystalline material sintering at 141° and melting at 146°-148°. The product has the formula

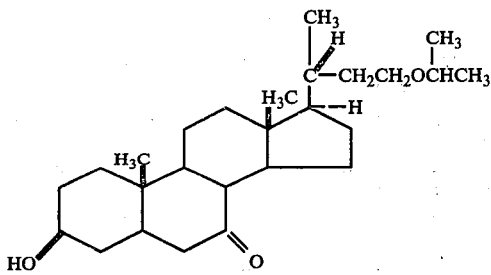

EXAMPLE 8

A. To a solution of 63 parts of 3β-(acetyloxy)-24-norchol-5-en-23-oic acid [J. Amer. Chem. Soc., 77, 1910 (1955)] in 1800 parts of tetrahydrofuran at −78° in a nitrogen atmosphere is slowly added, with stirring, a solution of 3 parts of borane in 180 parts of tetrahydrofuran. When the addition is complete, stirring under nitrogen is continued while the reaction mixture warms to room temperature, and for 2 hours thereafter, whereupon the mixture is poured into 15,000 parts of 5% hydrochloric acid. Approximately 1000 parts of sodium chloride is mixed in; and the precipitate which forms is separated by filtration, washed with water, dried in air, and taken up in dichloromethane. The dichloromethane solution is dried over magnesium sulfate and stripped of solvent by vacuum distillation. The residue is chromatographed on neutral alumina, using 5% acetate in benzene as developing solvent. Eluates are selected via thin layer chromatography which, upon evaporation of solvent and recrystallization of the residues from a mixture of 2-propanone and hexane, afford 3β-(acetyloxy)-24-norchol-5-en-23-ol melting at 157.5°-159°.

B. To a solution of 1 part of 3β-(acetyloxy)-24-norchol-5-en-23-ol in 45 parts of dichloromethane at −30° is added, with stirring, 35 parts of 2-methyl-1-propene followed by 1 part of a 1:1 complex of trifluoroborane and phosphoric acid. The resultant mixture is refluxed at 6° for 4 hours with continued stirring, then poured into approximately 600 parts of 5% ammonium hydroxide. Excess 2-methyl-1-propene is distilled off, and the distilland is filtered. Both the material filtered out and the filtrate are extracted with 1,1'-oxybisethane. The extracts are combined, dried over magnesium sulfate, and stripped of solvent by vacuum distillation. The residue is chromatographed on silica gel, using 2% ethyl acetate in benzene as developing solvent. Eluates are selected via thin layer chromatography which, upon evaporation of solvent and recrystallization of the residues from a mixture of 1,1'-oxybisethane and hexane, afford 3β-(acetyloxy)-23-(1,1-dimethylethoxy)-24-norchol-5-ene melting at approximately 134°-135°.

C. To a solution of 15 parts of pyridine in 340 parts of dichloromethane under a nitrogen atmosphere is added, with stirring at room temperature, 8 parts of chromium oxide. The resultant mixture is stirred at room temperature under nitrogen for ½ hour, whereupon a solution of 2 parts of 3β-(acetyloxy)-23-(1,1-dimethylethoxy)-24-norchol-5-ene in 60 parts of dichloromethane is stirred in. Stirring at room temperature under nitrogen is continued for 28 hours, at which point liquid supernatant is separated by decantation, residual solids are extracted with dichloromethane, the extract is combined with the supernatant, and solvent is removed from the combined liquids by vacuum distillation. The residue is extracted with hot 1,1'-oxybisethane, and the extract is filtered through diatomaceous earth. The filtrate is stripped of solvent by vacuum distillation; and the residue is chromatographed on silica gel, using 5% ethyl acetate in benzene as developing solvent. Eluates are selected via thin layer chromatography which, upon evaporation of solvent and recrystallization of the residues from a mixture of 1,1'-oxybisethane and methanol, afford 3β-(acetyloxy)-23-(1,1-dimethylethoxy)-24-norchol-5-en-7-one melting at approximately 169°-170°.

D. A mixture of 7 parts of 3β-(acetyloxy)-23-(1,1dimethylethoxy)-24-norchol-5-en-7-one, 5 parts of potassium bicarbonate, 400 parts of methanol, and 100 parts of water is heated at approximately 60° for 1 hour, then poured into 3000 parts of water. Sufficient sodium chloride is stirred into the resultant solution to saturate it, whereupon the solid which precipitates is isolated by filtration, washed with water, dried in air, and taken up in 1,1'-oxybisethane. The resultant solution is dried over magnesium sulfate and filtered through diatomaceous earth. The filtrate is stripped of solvent by vacuum distillation; and the residual yellow oil is chromatographed on silicic acid, using benzene and mixtures thereof with increasing amounts of ethyl acetate as developing solvent. Eluates are selected via thin layer chromatography which, upon evaporation of solvent and recrystallization of the residues from a mixture of 1,1'-oxybisethane and hexane, afford 3β-hydroxy-23-(1,1-dimethylethoxy)-24-norchol-5-en-7-one melting at 145°-147°. The product has the formula

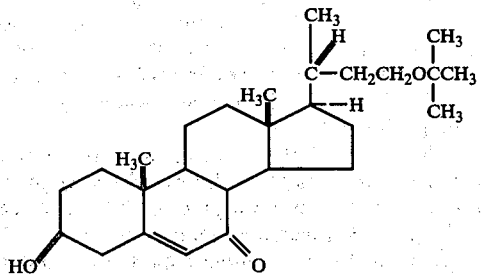

EXAMPLE 9

A mixture of 1 part of 3β-hydroxy-23-(1,1-dimethylethoxy)-24-norchol-5-en-7-one, 5 parts of propanoyl chloride, and 10 parts of pyridine is allowed to stand at room temperature overnight, then poured into 120 parts of 5% hydrochloric acid. The resultant mixture is extracted with 1,1'-oxybisethane. The extract is dried over magnesium sulfate and stripped of solvent by vacuum distillation. The residue is 3β-(1-oxopropoxy)-23-(1,1-dimethylethoxy)-24-norchol-5-en-7-one, having the formula

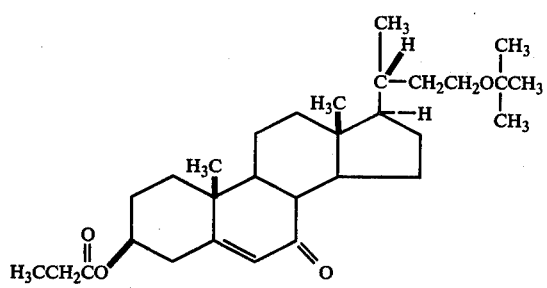

What is claimed is:

1. A compound of the formula

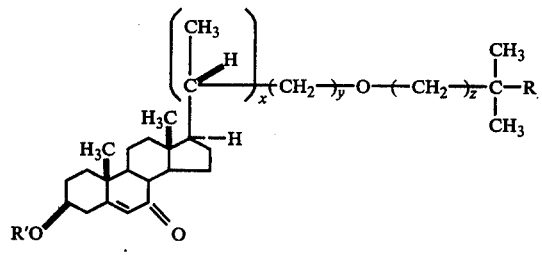

wherein R represents hydrogen or methyl; R' represents hydrogen or 1-oxoalkyl of fewer than 9 carbons; $x$ represents 0 or 1; $y$ represents 0, 1, or 2; $z$ represents 0, 1, 2, or 3; the sum of the integers represented by $x$, $y$, and $z$ is 3; and $x$ represents 0 only when $y$ represents 0.

2. A compound according to claim 1 having the formula

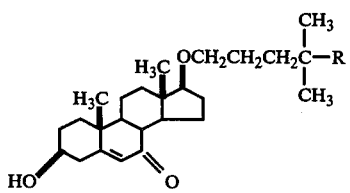

wherein R represents hydrogen or methyl.

3. A compound according to claim 1 which is 3β-hydroxy-17β-[(4-methylpentyl)oxy]androst-5-en-7-one.

4. A compound according to claim 1 having the formula

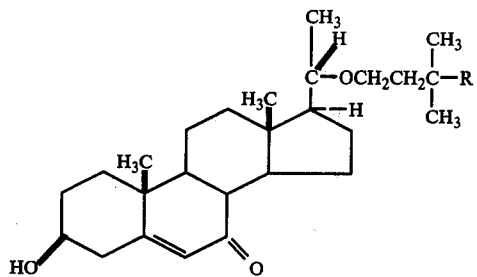

wherein R represents hydrogen or methyl.

5. A compound according to claim 1 which is 20S-(3-methylbutoxy)-3β-hydroxypregn-5-en-7-one.

6. A compound according to claim 1 having the formula

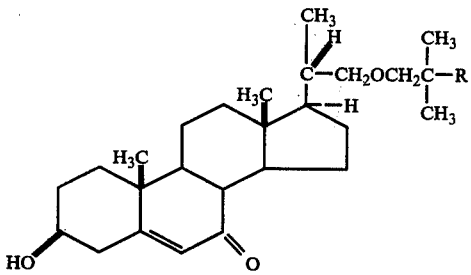

wherein R represents hydrogen or methyl.

7. A compound according to claim 1 which is 3β-hydroxy-20S-methyl-22-(2-methylpropoxy)pregn-5-en-7-one.

8. A compound according to claim 1 which is 22-(2,2-dimethylpropoxy)-3β-hydroxy-20S-methoxypregn-5-en-7-one.

9. A compound according to claim 1 which is

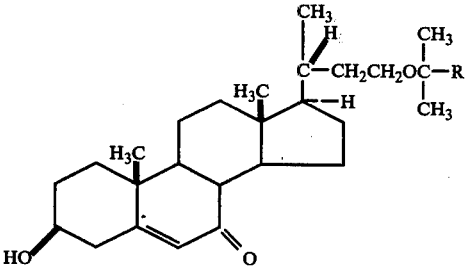

wherein R represents hydrogen or methyl.

10. A compound according to claim 1 which is 3β-hydroxy-23-(1-methylethoxy)-24-norchol-5-en-7-one.

* * * * *